United States Patent [19]
Blechman

[11] Patent Number: 5,205,736
[45] Date of Patent: Apr. 27, 1993

[54] MAGNETIC ORTHODONTIC APPLIANCE

[76] Inventor: Abraham M. Blechman, 153 Lester Dr., Tappan, N.Y. 10983

[21] Appl. No.: 858,340

[22] Filed: Mar. 26, 1992

[51] Int. Cl.⁵ .............................. A61C 3/00
[52] U.S. Cl. ........................ 433/18; 433/22
[58] Field of Search ................. 433/18, 19, 22

[56] References Cited

U.S. PATENT DOCUMENTS

| | | | |
|---|---|---|---|
| 3,353,271 | 11/1967 | Blechman | 433/18 |
| 4,457,707 | 7/1984 | Smiley et al. | 433/18 |
| 4,484,895 | 11/1984 | Smiley et al. | 433/215 |
| 4,508,505 | 4/1985 | Smiley et al. | 433/18 |
| 4,526,539 | 7/1985 | Blechman et al. | 433/18 |
| 4,595,361 | 6/1986 | Blechman et al. | 433/18 |
| 5,066,224 | 11/1991 | Block et al. | 433/18 |

Primary Examiner—John J. Wilson

[57] ABSTRACT

An orthodontic appliance for intraorally distalizing teeth without patient compliance, comprising a pair of small complementary permanent magnetic elements slidably mounted on a single common sectional wire in an arrangement to repel one another, and means for maximally reengaging the magnetic elements along the sectional wire. This arrangement avoids undesirable eccentric magnetic movement and maximizes control of the repelling horizontal magnetic forces.

9 Claims, 3 Drawing Sheets

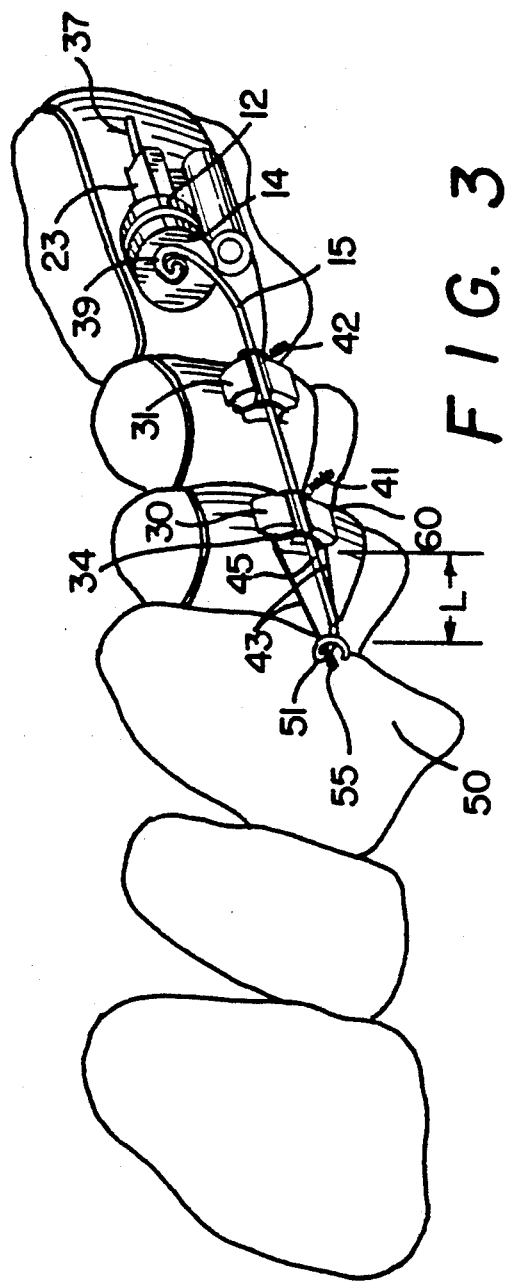
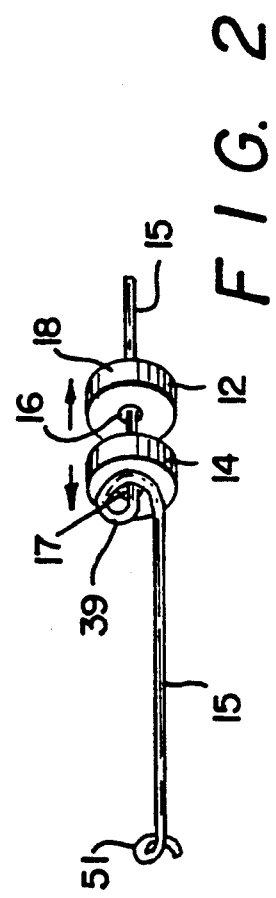

MAGNETIC ORTHODONTIC APPLIANCE

FIELD OF THE INVENTION

The invention relates to an orthodontic appliance incorporating magnets to selectively move human dentition intraorally without the need for patient compliance or assistance.

BACKGROUND OF THE INVENTION

Moving teeth intraorally using forces generated from permanent magnets has had little commercial success to date, primarily due to the complexity of conventional permanent magnet appliance systems, their large dimensions, their high cost, and their dependence, at least in part, upon patient compliance, which otherwise results in the patient playing with the appliance and possibly inactivating or destroying it because of its large dimensions and discomfort. Attachment of a known permanent magnet appliance to the dentition in the upper and lower jaws requires the use of either the main or the sectional arch wires, or both, in an unwieldy arrangement which is difficult to adjust properly and requires patient compliance to avoid inactivation or destruction. The magnetic force developed between the magnetic elements is controlled by bending the wires, to which the elements are connected in a precise way, so that the poles of the magnets are kept aligned to avoid eccentric movement. This has proven to be cumbersome in practice. Moreover, most conventional permanent magnet systems presently in use rely on a rectangular-shaped magnetic element which is encased in a steel sleeve. The sleeve is connected to the sectional wire through a separate fitting, such as, for example, an elongated tube projecting from the steel sleeve. This arrangement inherently results in a physical offset between the center of the magnet and the sectional wire, which creates a rotational bending moment tending to rotate the magnet about the sectional wire. To prevent buccal torquing in such an arrangement and to maintain proper alignment of the poles of the magnetic elements relative to one another, it was necessary to use a sectional wire of rectangular cross-section with a corresponding rectangular fitting, all of which is nonstandard. This resulted in a complex and costly permanent magnet appliance. Other magnetic designs use several large disk-shaped magnets that are uncomfortable, costly, and required considerable patient compliance, resulting in a high degree of non-acceptance.

Because of the recognized clinical advantages of permanent magnet orthodontics, there has been a long-sought need for an orthodontic appliance using small magnets, which can be implemented in a simple, unwieldy, and less costly manner in the treatment of orthodontic cases requiring molar or premolar distalization, which does not depend upon any patient compliance or assistance.

SUMMARY OF THE INVENTION

The orthodontic appliance of the present invention broadly comprises a pair of complementary cylindrical permanent magnetic elements, each having an opening axially extending through the symmetrical center thereof, and an orthodontic sectional wire having cross-sectional dimensions smaller in size than the opening of each element for slidably mounting said elements along said wire in a mesial and distal relationship, with the elements mounted upon said wire to repel one another, means for positioning the mesial magnetic element in substantial abutting engagement to the distal magnetic element, with the distal magnetic element abutting the tooth or teeth to be moved distally relative to its proximal teeth, and means for maximally reengaging the magnetic elements along said common sectional wire as movement occurs.

The simplicity of the orthodontic magnetic appliance of the present invention eliminates the need to enclose the magnetic elements in separate sleeve-type modules, and eliminates the need to conjointly use a separate main arch wire on the upper and/or lower jaw, respectively. Moreover, the magnetic appliance may now be readily mounted to the dentition using standard orthodontic mounting brackets, molar tubing, and standard orthodontic wires. Another advantage of the orthodontic appliance of the present invention is its simplicity in moving molar teeth distally on one arch independent of the other arch, or simultaneously on both the upper and lower jaws, respectively. Moreover, the teeth are moved distally without any surgical intervention and without the need for patient compliance or assistance.

BRIEF DESCRIPTION OF THE DRAWINGS

Other advantages of the present invention will become apparent from the following detailed description of the invention when read in conjunction with the accompanying drawings of which:

FIG. 2 is an exploded view in perspective of the cylindrical magnets of FIG. 1, shown mounted in common on a single sectional wire;

FIG. 3 is an enlarged view of the area in FIG. 1 showing the orthodontic appliance of the present invention mounted to the posterior teeth;

DETAILED DESCRIPTION OF THE INVENTION

Figure 1:
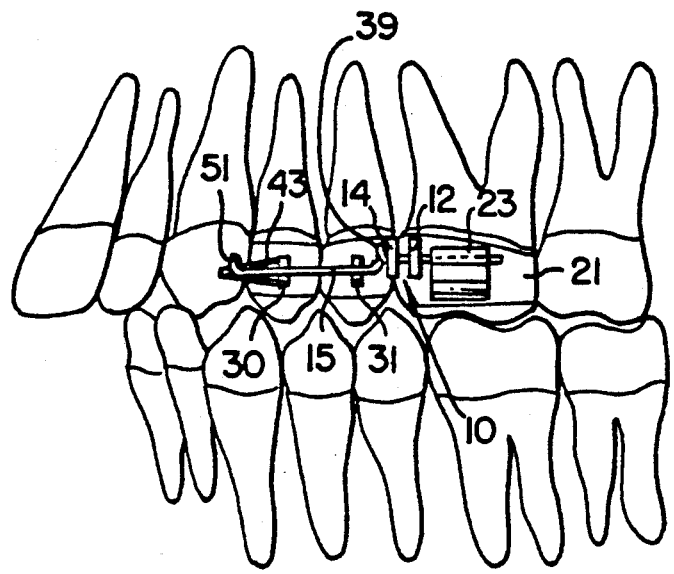
FIG. 1 is an elevational view of the upper and lower jaw of typical human dentition viewed from the buccal side, with the orthodontic appliance of the present invention connected to selected posterior teeth in the upper jaw.

Referring to the drawings and, in particular, to FIGS. 1 through 5, inclusive, the orthodontic appliance of the present invention is shown comprising an assembly (10), including a pair of complementary magnetic elements (12) and (14) mounted on a single sectional arch wire (15), in coaxial alignment with the longitudinal axis of the magnetic elements. The sectional wire (15) is a conventional orthodontic, preferably round, steel wire of typically 0.016-inch or 0.018-inch diameter. The magnetic elements (12) and (14) are permanent magnets which are of cylindrical geometry, as shown in FIGS. 2 and 3, each having an opening (16) and (17), respectively, which extends through the center of each element along the longitudinal axis thereof. The diameter of each opening (16) and (17) is slightly larger than the diameter of the sectional arch wire (15) to permit the magnets (12) and (14) to freely slide along the arch wire (15). The magnets (12) and (14) are mounted on the arch wire (15) to repel one another, i.e., with their repelling pole faces (18) and (19) abutting one another. Although the sectional wire (15) is preferably round, other geometries, such as square or rectangular, may be used. If a square sectional wire (15) is used, it is, of course, preferred to use a corresponding geometry for the central openings (16) and (17). Moreover, although the permanent magnetic elements (12) and (14) are cylindrical, they need not be of identical diameter.

Figure 5:
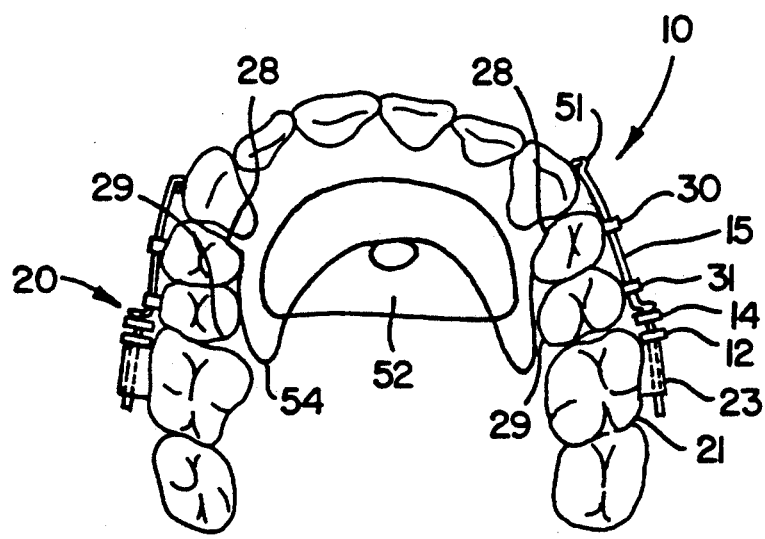
FIG. 5 is an occlusal view of the teeth of the upper jaw of FIG. 1, showing the orthodontic appliance of the present invention symmetrically mounted on opposite sides of the upper jaw in conjunction with an anchorage palatal retainer.

The assembly (10) is preferably buccally mounted upon either the upper or lower arch of the teeth on one side thereof, with an equivalent assembly (20), as shown in FIG. 5, symmetrically mounted on the opposite buccal side of the same arch to distalize selected posterior teeth, such as a first molar tooth or first and second molar teeth at the same time. The assemblies (10) and (20) can also be mounted and used on the lingual side of the same teeth.

Figure 4:
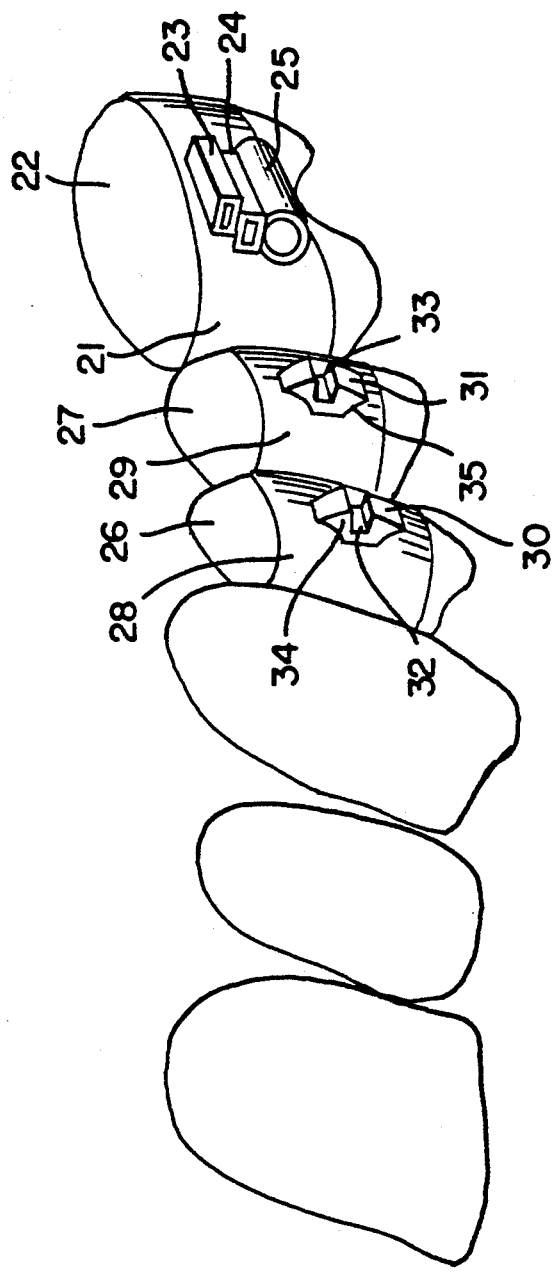
FIG. 4 is another view, similar to FIG. 3, showing the bracket and band connections prior to attachment of the magnet and sectional wire assembly.

To affix each assembly (10) and (20) to the dentition, it is, at first, necessary to prepare the teeth to receive the assembly by mounting appropriate orthodontic brackets and bands. As shown in FIG. 4, a molar band (21) is fitted upon the first molar tooth (22). The molar band (21) is a commercially available item which can be purchased with edgewise buccal tubes (23) and (24), and a headgear tube (25) which is prewelded to the band (21). It is conventional for the upper edgewise tube (23) to extend buccally from the band (21). The upper edgewise tube (23) is hollow and is preferably guided by the sectional wire (15) in the operation of the orthodontic appliance of the present invention, as will be hereafter explained in greater detail. The hollow edgewise tube (24) and the hollow headgear tube (25) may remain temporarily nonfunctional and used later in the treatment for other orthodontic purposes independent of this application. The bicuspid teeth (26) and (27) have similar bands (28) and (29) mounted thereon with standard edgewise brackets (30) and (31) prewelded to the bands. The brackets (30) and (31) include slotted openings (32) and (33) adapted to receive the sectional wire (15), and are configured with conventional wings (34) and (35) extending from the openings (32) and (33). The wings (34) and (35) permit the use of conventional ligature wires. Ligature wires, as will be explained hereafter, are used to secure and hold the sectional wire (15) in place within the brackets (30) and (31).

The magnetic elements (12) and (14) are mounted on the sectional wire (15), with the distal end (37) of the sectional wire (15) slidably inserted into the edgewise tube (23). The sectional wire (15) is bent, preferably in advance, to form a loop (39) which secures the mesial side of the magnetic element (14), so the magnetic element (14) is fixed in position mesially, relative to the magnetic element (12). The sectional wire (15) is then inserted into the slotted openings (32) and (33), and ligated to the brackets (30) and (31) using standard ligature wires (41) and (42), respectively. The opposite side (45) of the sectional wire (15), which extends mesially from the brackets (30) and (31), terminates in a free and open end (50). It is preferred to bend the open end (50) of the sectional wire (15) into a loop (51). It is also preferred to wind another ligature wire (43) around the wing (34), and thread this wire through the mesial loop (51), so that the sectional wire (15) is readily movable distally when tightened by the orthodontist, to readily reposition the magnetic elements closer together after they have separated due to the distal movement of the molar tooth or teeth. When the mesial ligature wire (43) through the mesial loop (51) is tightened, it causes the entire sectional wire (15) to slide distally. The bend or loop (39) in the sectional wire (15) pushes the magnetic element (14) back into an active position adjacent to the magnetic element (12). By sliding the sectional wire (15) distally, the edgewise tube (23) now has more guide wire to slide on. This prevents the molar tooth, which is being distalized, from causing the edgewise tube (23) from running off the sectional guide wire (15) and eliminates the need to replace the sectional wire (15) with another wire when reactivating the magnetic appliance. Furthermore, by limiting the magnetic forces to only one arch, rather than by generating force by the interaction between the upper and lower jaws, avoids the need to wire both jaws, as is now practiced.

To fully utilize the magnetic force in moving teeth distally, it is advantageous to use an enlarged Nance palatal button (52) as additional anchorage to prevent movement of all teeth mesial to the molars. The palatal button (52) is connected with a wire (54) to the first and second bicuspid bands (28) and (29) on the lingual side thereof. The wire (54) may be secured to the bands (28) and (29) by soldering them together into an integral unit before placement into the mouth. The Nance palatal button (52) provides anchorage to resist the reactive force of the mesial repelling magnetic element in each of the assemblies (10) and (20), respectively.

In the assembled position, the magnetic element (12) abuts the upper edgewise tube (23), and the distal end (37) of the sectional wire (15) projects out slightly from the distal end of the hollow edgewise tube (23) to prevent irritation of the buccal mucosa. In this position, the magnetic elements (12) and (14) are physically as close to contact as possible, with minimal air gap, so that the magnetic repulsion force between the magnetic elements is at maximum. As the molar tooth (or teeth) distalizes, the edgewise tube (23) moves with the molar teeth rearward, guided by the sectional wire (15). After a reasonable displacement occurs between the magnetic elements, the appliance must be reactivated by the orthodontist. As explained earlier, this is accomplished by advancing the entire sectional wire (15) distally simply by tightening the pigtailed free end of the mesial ligature wire running through the mesial loop (51).

The dimensions of the magnetic elements (12) and (14) and their energy product will determine the force of repulsion between the magnets. By limiting the thickness of the circular magnetic elements to no more than about 2 to 2.5 millimeters, the correct geometric configuration for force generation is attained, and also the inconvenience of the patient is minimized. The magnetic elements (12) and (14) are preferably composed of a magnetized stable, high energy product alloy, having an axis of polarization coaxial with its longitudinal axix. It is preferred to coat the entire outside surface of each magnetic element (12) and (14), including the hole, with a biocompatible material, such as Parylene-C, manufactured by Union Carbide Corporation, a coating composition of poly-p-xylene with a single chlorine atom replacing a hydrogen atom. The biocompatible coating prevents any contaminants from leaching into the mouth.

Because the magnetic elements (12) and (14) are slidably mounted on a common sectional wire (15) along the symmetrical center of each element, the force of repulsion between the opposing pole faces (18) and (19) is essentially unidirectional and parallel to its longitudinal axis. Moreover, eccentric vector forces are cancelled out, and no rotational forces exist between the elements to generate torque. Accordingly, the magnetic elements (12) and (14) are limited to unidirectional movement guided by the sectional wire (15). The force of repulsion decreases as the gap between the pole faces increases, in a relationship somewhere between the square of the distance separating the elements and linear. It is, accordingly, necessary to reactive the elements by incrementally bringing them into closer contact after a predetermined gap separation has developed. The length ("L") of sectional arch wire (15) extending from the mesial edge (60) of the bracket (30) on the first bicuspid to the mesial loop (51) determines the maximum distance of molar distalization (approximately 7 mm). For example, in a full class II malocclusion, approximately 5 mm of molar distalization is required to achieve a class I molar relationship with the lower molar. By over-correcting, e.g., distalizing 6 mm to 7 mm, the relapse tendency is minimized. This magnetic system is capable of this type of movement. Furthermore, the control of the rearward movement of the teeth occurs without any patient assistance or compliance.

What is claimed:

1. An orthodontic appliance for distalizing a posterior tooth or teeth without surgical extraction, comprising a plurality of anchoring bands adapted to be mounted to certain selected teeth on a single arch of a patient inclusive of the posterior tooth or teeth to be distalized, and at least one proximal tooth anterior thereto; an edgewise member affixed to the anchoring band on the posterior tooth to be distalized, bracket means affixed to the other band(s); an orthodontic sectional wire extending from said edgewise member to said bracket means; and a pair of permanent magnets of cylindrical geometry, each having an opening axially extending through the symmetrical center thereof, with said magnets slidably mounted on said sectional wire through said central openings in an arrangement to repel one another, with the magnet on the distal side of said sectional wire abutting said edgewise member, and with the other magnet in close proximity thereto, and means for securing said magnetic on the mesial side of said sectional wire relative to the proximal tooth or teeth supporting said bracket means.

2. An orthodontic appliance, as claimed in claim 1, wherein said orthodontic sectional wire is of cylindrical geometry, and wherein said opening in each magnet is circular in geometry, with said magnets mounted on said sectional wire so that their longitudinal axes are coaxial.

3. An orthodontic appliance, as claimed in claim 2 wherein said edgewise member is a hollow tube with said sectional wire slidably mounted within said tube.

4. An orthodontic appliance, as claimed in claim 3, wherein each bracket has a slot for receiving said sectional wire.

5. An orthodontic appliance, as claimed in claim 4, further comprising means for ligating said sectional wire to said bracket(s) affixed to the bands on said proximal teeth.

6. An orthodontic appliance, as defined in claim 5, wherein said sectional wire has a bend in the form of a loop for engaging said other magnet on the mesial side thereof to secure said magnet from moving mesially, and with said sectional wire terminating in a mesial free end.

7. An orthodontic appliance, as defined in claim 6, further comprising means for engaging the mesial free end of said sectional wire to enable the sectional wire to be adjusted distally as molar movement occurs.

8. An orthodontic appliance, as defined in claim 7, wherein said mesial free end of said sectional wire is bent in the form of a loop.

9. An orthodontic appliance, as defined in claim 8, further comprising a Nance palatal button and means for connecting said Nance palatal button to said anchoring bands on said proximal tooth or teeth for providing anchorage, to prevent movement of the teeth mesial to the posterior teeth to be distalized.

* * * * *